United States Patent [19]

Kasuya

[11] Patent Number: 4,985,020

[45] Date of Patent: Jan. 15, 1991

[54] NEEDLE CAP FOR INJECTOR, GUIDE FOR NEEDLE CAP AND GRIP FOR NEEDLE CAP

[76] Inventor: Shiro Kasuya, 4 Nakashin-machi, Gifu-shi, Gifu-ken, 500, Japan

[21] Appl. No.: 369,116

[22] Filed: Jun. 21, 1989

[30] Foreign Application Priority Data

Jun. 24, 1988 [JP] Japan .................................. 63-157751

[51] Int. Cl.⁵ ............................................... A61M 5/32
[52] U.S. Cl. ..................................... 604/192; 604/263
[58] Field of Search ................ 604/192, 198, 263, 187

[56] References Cited

U.S. PATENT DOCUMENTS 4,826,488  5/1989  Nelson et al. ........................ 604/192

FOREIGN PATENT DOCUMENTS 2620341  3/1989  France ................................. 604/263

Primary Examiner—John D. Yasko
Attorney, Agent, or Firm—Kareem M. Irfan

[57] ABSTRACT

A needle cap adapted to cover a needle of an injector. The needle cap comprises a cylindrical cap body which has an opening at its longitudinal end, and a gripped portion provided on the cap body to extend substantially in the radial direction of the cap body. The cap body further comprises a guiding portion which is provided on a part of the circumference of the opening at the longitudinal end of the cap body and extends substantially in the longitudinal direction of the cap body. The gripped portion and guiding portion are formed integrally with the cap body, or composed of a leaf attached to the cap body, or formed separately from the cap body so as to be detachable to the cap body.

4 Claims, 2 Drawing Sheets

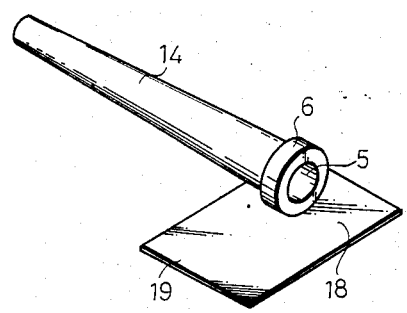
FIG. 4
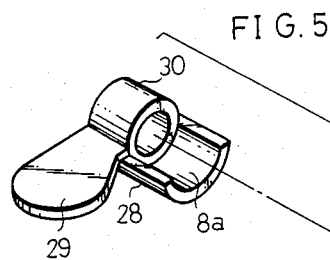
FIG. 5
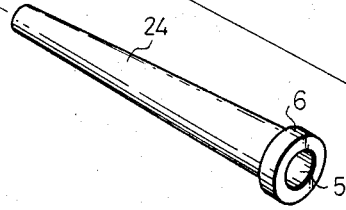
FIG. 6
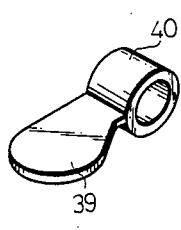
FIG. 7
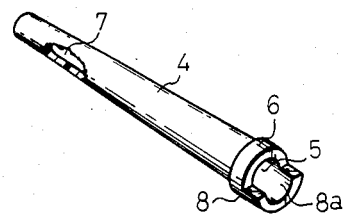
FIG. 8
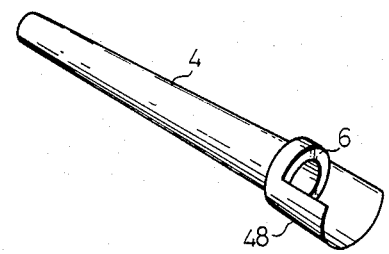
FIG. 9
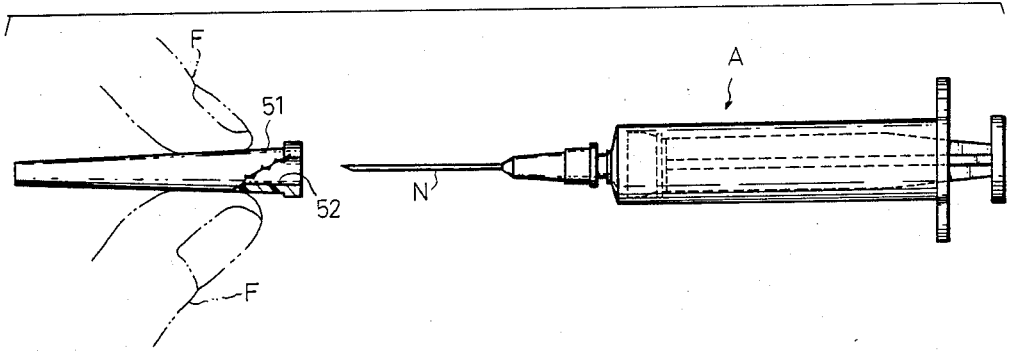

NEEDLE CAP FOR INJECTOR, GUIDE FOR NEEDLE CAP AND GRIP FOR NEEDLE CAP

FIELD OF THE INVENTION

The present invention relates to a needle cap covering a needle of an injector, a guide for needle cap and a grip for needle cap each fitted on the needle cap.

DESCRIPTION OF THE RELATED ART

A usual needle cap covering a needle of a disposable injector is, for example, shown in FIG. 9. A needle cap 51 has a shape of a bottomed tube with the rear end (right end in the FIG. 9) thereof opened. In the use of the needle cap 51 after injection, a user catches the needle cap 51 with fingers F of one hand while keeping hold of an injector A with the other hand not shown. Then the user positions the opening 52 of the needle cap 51 in relation to a needle N of the injector A, and puts the needle cap 81 on the needle N.

However, it is difficult to position the opening 52 in relation to the needle N since the opening 52 of the needle cap 51 has a small area. Subsequently, there is a fear that, when the user brings the needle cap 51 close to the needle N, the finger F catching the needle cap 51 should touch by accident and be injured by the tip of the needle N. Particularly, in case pathogene which a patient carries have stuck to the needle N, it is apprehended that the user should catch disease due to the pethogene when the finger F touches and is injured by the tip of the needle N.

SUMMARY OF THE INVENTION

An object of the present invention is to provide a needle cap, a guide for needle cap and a grip for needle cap which eliminate any fear that a finger of a user taking the needle cap should touch the tip of a needle by accident when the user puts the needle cap on the needle.

In order to attain the above object, the needle cap of the present invention comprises a cylindrical cap body having an opening at its longitudinal end and covering a needle; and a gripped portion provided on the cap body to extend substantially in the radial direction of the cap body.

Other and further objects of this invention will become obvious upon an understanding of the illustrative embodiments about to be described or will be indicated in the appended claims, and various advantages not referred herein will occur to one skilled in the art upon an employment of the invention in practice.

BRIEF DESCRIPTION OF THE DRAWINGS

FIG. 4 is a schematic view showing a modification of a needle cap;

FIG. 5 is an exploded schematic view showing a guide for needle cap;

FIG. 6 is a schematic view showing a grip for needle cap;

FIGS. 7 and 8 are schematic views respectively showing modifications of guides for needle cap; and FIG. 9 is a front view showing a needle cap of the related art.

DESCRIPTION OF THE PREFERRED EMBODIMENTS

A first embodiment of the present invention, which is embodied in a needle cap adapted to cover a needle of a disposable injector, will be explained hereunder in accordance with FIGS. 1 to 3.

Figure 1:
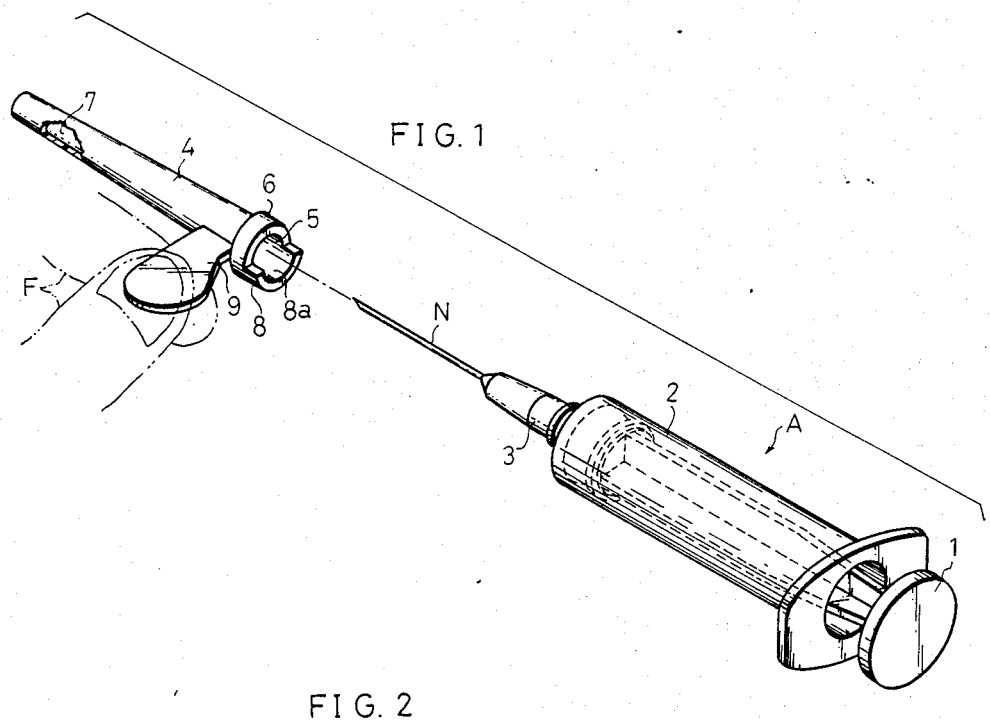
FIG. 1 is a schematic view showing a state in which a needle cap of a first embodiment of the present invention is covering a needle of an injector.
Figure 2:
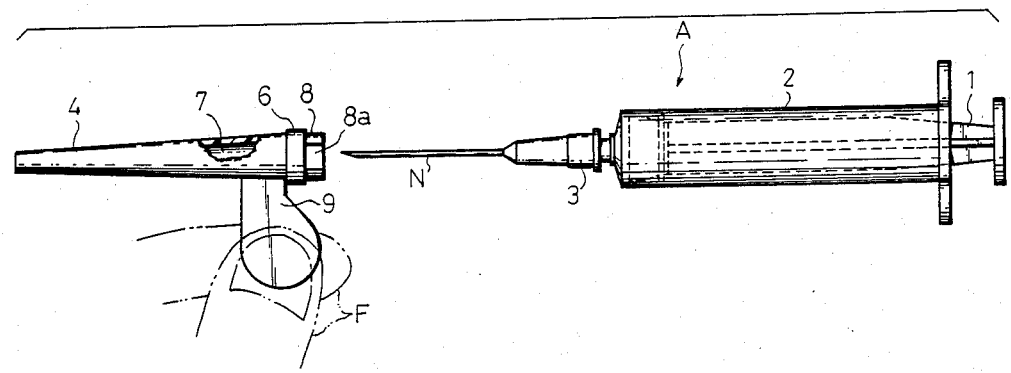
FIG. 2 is a front view of FIG. 1.

As shown in FIGS. 1 and 2, an injector A, to which the needle cap of the present embodiment is fitted, comprises a piston and a cylinder which slidably accommodates the cylinder 1. A supporting member 3 provided with a needle N is attached to a leading end (left end in FIG. 2) of the cylinder 2.

The needle cap made of, for example, a synthetic resin is put on the supporting member 3. A cylindrical cap member 4, which constitutes a main part of the needle cap, has a bottom at its front end and an opening at its rear end, and defines therein an accommodating recess which is able to accommodate the needle N. A fitted portion 6 is formed at the rear end of the cap body 4 and has a larger thickness than the cap body 4. The fitting portion 6 has an inner diameter substantially as large as that of the outer diameter of the supporting member 3 so as to be fittable onto the same supporting member 3.

A guiding portion 8 having a semicircular section is integrally formed on the lower half part of the fitting portion 6 so as to protrude rearwardly therefrom so that the opening 8 of the cap body 4 is able to be positioned in relation to the needle N by getting an inner surface 8a of the guiding portion 8 in contact with one side of the needle N. A thin plate like gripped portion 9 extends from the outer periphery of the cap body 4 in the radial direction thereof so that the user can grip the portion 9. The cap body 4, guiding portion 8 and gripped portion 9 constitute the needle cap.

Hereunder described are the operation and effects of the needle cap of the present embodiment constructed as mentioned above.

FIGS. 1 and 2 respectively show a state in which the needle cap is covering the needle N of the injector A after injection. In this state, the user grips the gripped portion 9 with the fingers F of one hand while holding the injector A with the other hand. Then the user brings the needle cap close to the needle N and positions the opening 5 to the needle N. In the present embodiment, since the guiding portion 8 of semicircular section is formed at the opening 5, the user can easily position the opening 5 to the needle N by putting the inner surface 8a of the guiding portion 8 on the leading end portion of the needle N, so that there is no fear that the finger F should touch the needle N.

Figure 3:
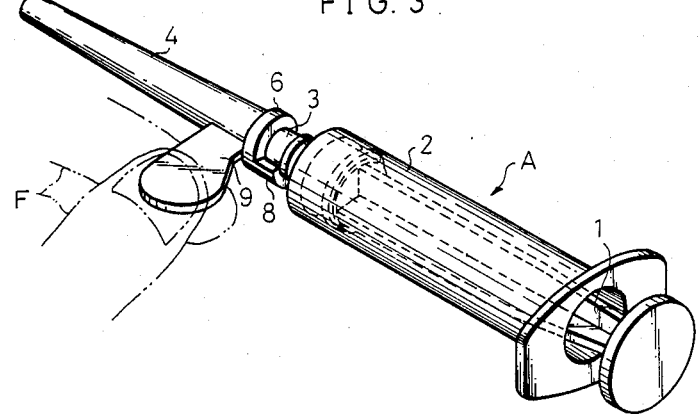
FIG. 3 is a schematic view showing a state in which the needle cap has covered the needle of the injector.

Next, the user moves the needle cap toward the supporting member 3 of the injector A while holding the gripped portion, and puts the fitting portion 6 of the needle cap on the supporting portion 3 of the injector A as shown in FIG. 3, thereby to cover the needle N by the needle cap. In moving the needle cap toward the needle N as described above, the fingers F holding the gripped portion 9 are away from the opening 8, since the gripped portion 9 is formed on the cap body 4 such as to extend in the radial direction thereof. Therefore, even in case the opening 5 has not been exactly positioned in relation to the needle N, it is never apprehended that the finger F should touch the needle N.

As a result, in the use of the needle cap of the present embodiment, even if pathogene of a patient have adhered to the needle N in injection, there is no possibility that the user should catch the disease of the patient, so that there arises no sanitary problem, contrary to the needle cap of the related art.

The needle cap of the present invention may be modified as follows. For example, as shown in FIG 4, a guiding portion 18 and a gripped portion 19 may be made of a leaf composed of a sheet of paper, synthetic resin, etc., and be adhered to the needle cap body 14 via adhesive agent, adhesive double coated tape and so on.

Further, the present invention may be embodied into a guide for needle cap fittable to a needle cap body 24, for example as shown in FIG. 5. The same guide comprises a cylindrical connecting portion 30 fittable to the needle cap body 24, and a gripped portion 29 and a guide portion 28 each formed integrally with the connecting portion 30. The guide for needle cap has similar effects to those of the above mentioned embodiment.

Moreover, the present invention may be embodied into a grip for needle cap fittable to a needle cap body 34, for example as shown in FIG. 6. The same grip comprises a cylindrical connecting portion 40 fittable to the needle cap body 34 and a gripped portion 39 integrally formed with the connecting portion 40.

Furthermore, the present invention may be embodied into a needle cap consisting of the guide portion 8 without provision of any gripped portion, for example as shown in FIG. 7. In this case, the guide portion 8 may be formed separately from the cap body 4 so as to be detachable to the cap body 4. Otherwise, as shown in FIG. 8, an adhesive tape may be adhered on the outer periphery of the fitting portion 6 and then have the upper part thereof removed so as to form a guide portion 48.

As many apparently widely different embodiments of this invention may be made without departing from the spirit and scope thereof, it is to be understood that the invention is not limited to the specific embodiments thereof except as defined in the appended claims.

What is claimed is:

1. A needle cap adapted to cover a needle of an injector, comprising:
   a cylindrical cap body for covering said needle and having an opening at its longitudinal end;
   a grip portion provided on said cap body and extending substantially in the radial direction of said cap body; and
   a guiding portion provided on a part of the circumference of said cap body opening and extending substantially in the longitudinal direction of said cap body, said guiding portion including a needle support surface extending therefrom for a length shorter than that of said needle, whereby a needle may be positioned onto the needle support surface by movement along a radial direction thereof, and subsequently moved inwardly along a longitudinal direction thereof into said cap body through said opening, said guiding portion having a substantially arcuate section and said needle support surface being substantially wider than the diameter of said needle.

2. A needle cap according to claim 1, wherein said gripped portion is formed integrally with said cap body.

3. A needle cap adapted to cover a needle of an injector, comprising:
   a cylindrical cap body having an opening at its longitudinal end and covering said needle; and
   a guiding portion provided on a part of the circumference of said opening at said longitudinal end of said cap body, said guiding portion extending substantially in the longitudinal direction of said cap body, said guiding portion having a substantially arcuate section with an inner needle support surface having a width substantially larger than the diameter of said needle, said needle support surface extending from said guiding portion for a length shorter than that of said needle whereby a needle may be positioned onto the needle support surface by movement along a radial direction thereof, and subsequently moved inwardly along a longitudinal direction thereof into said cap body through said opening.

4. A needle cap according to claim 3, wherein said guiding portion is formed integrally with said cap body.

* * * * *